United States Patent
Stamboulis et al.

(10) Patent No.: US 10,501,495 B2
(45) Date of Patent: Dec. 10, 2019

(54) ANTIMICROBIAL SURFACE

(71) Applicants: The University of Birmingham, Birmingham (GB); The Secretary of State for Defence of the United Kingdom of Great Britain and Northern Ireland, London (GB)

(72) Inventors: Artemis Stamboulis, Birmingham (GB); Felicity Jane de Cogan, Birmingham (GB); Robert Scott, Birmingham (GB); Anna Frances Acushia Peacock, Birmingham (GB)

(73) Assignees: The University of Birmingham, Birmingham (GB); The Secretary of State for Defence of the United Kingdom of Great Britain and Northern Ireland, London (GB)

( * ) Notice: Subject to any disclaimer, the term of this patent is extended or adjusted under 35 U.S.C. 154(b) by 390 days.

(21) Appl. No.: 15/119,634

(22) PCT Filed: Feb. 25, 2015

(86) PCT No.: PCT/GB2015/050544
§ 371 (c)(1),
(2) Date: Aug. 17, 2016

(87) PCT Pub. No.: WO2015/128643
PCT Pub. Date: Sep. 3, 2015

(65) Prior Publication Data
US 2017/0057998 A1    Mar. 2, 2017

(30) Foreign Application Priority Data
Feb. 25, 2014  (GB) .................... 1403268.4

(51) Int. Cl.
| | | |
|---|---|---|
| *C07K 7/08* | (2006.01) | |
| *A61L 27/54* | (2006.01) | |
| *C07K 17/14* | (2006.01) | |
| *A01N 25/08* | (2006.01) | |
| *A01N 47/44* | (2006.01) | |
| *C07K 14/00* | (2006.01) | |

(52) U.S. Cl.
CPC .............. *C07K 7/08* (2013.01); *A01N 25/08* (2013.01); *A01N 47/44* (2013.01); *A61L 27/54* (2013.01); *C07K 14/001* (2013.01); *C07K 17/14* (2013.01); *A61L 2300/25* (2013.01); *A61L 2300/404* (2013.01); *A61L 2420/02* (2013.01)

(58) Field of Classification Search
CPC ..... A01N 25/08; A01N 47/44; A61L 2300/25; A61L 2300/404; A61L 2300/606; A61L 2420/02; A61L 27/54; A61L 31/16; C07K 14/001; C07K 14/4723; C07K 17/08; C07K 17/14; C07K 2319/20; C07K 7/08
See application file for complete search history.

(56) References Cited

U.S. PATENT DOCUMENTS

| | | | | |
|---|---|---|---|---|
| 7,550,430 | B2 * | 6/2009 | Keeler | ................... 514/1.1 |
| 2003/0176652 | A1 * | 9/2003 | McCray, Jr. | ....... C07K 14/4723 530/350 |
| 2004/0121939 | A1 | 6/2004 | Diana | |
| 2009/0099533 | A1 * | 4/2009 | Montelaro | ............. A61K 38/08 604/265 |

FOREIGN PATENT DOCUMENTS

| | | |
|---|---|---|
| CN | 1021439 A | 7/2008 |
| EP | 2399618 A | 12/2011 |
| WO | WO2008/093058 A2 | 8/2008 |
| WO | WO2013/183048 A | 12/2013 |

OTHER PUBLICATIONS

Townsend et al. Antimicrobial peptide coatings for hydroxyapatite: electrostatic and covalent attachment of antimicrobial peptides to surfaces. J. R. Soc. Interface, vol. 15, 20160657, pp. 1-11. (Year: 2017).*
Materials that Cause Static Electricity. Materials that Cause Static Electricity accessed online at https://jh399.k12.sd.us/DailyAssign/Physics/ch7materialstaticelec.pdf on Feb. 26, 2019, page (Year: 2019).*
McEwan et al. Harnessing the power of cell-penetrating peptides: Activatable carriers for targeting systemic delivery of cancer. Wiley Interdiscip Rev Nanomed Nanobiotechnol, 2014, vol. 5, No. 1, pp. 1-26. (Year: 2014).*
Kyle V. Holmberg, et al: "Bio-inspired stable antimicrobial peptide coatings for dental applications", Acta Biomaterialia, vol. 9, No. 9, Jun. 19, 2013, pp. 8224-8231.
Masao Yoshinari, et al., "Prevention of biofilm formation on titanium surfaces modified with conjugated molecules comprised of antimicrobial and titanium-binding peptides", Biofouling, vol. 26, No. 1, Oct. 16, 2009,pp. 103-110.
Matthew B. Murphy, et al., "Synthesis and in Vitro Hydroxyapatite Binding of Peptides Conjugated to Calcium-Binding Moieties", Biomacromolecules, vol. 8, No. 7, Jul. 1, 2007, pp. 2237-2243.
Kashiwagi K, et al., "Directionai BMP-2 for functionalizatien of titanium surfaces", Biomaterials, Elsevier Science Pubilshers BV, Barking, GB, vol. 30, No. 6, Feb. 1, 2009, pp. 1166-1175.

(Continued)

*Primary Examiner* — Marcela M Cordero Garcia
(74) *Attorney, Agent, or Firm* — Brooks Kushman P.C./LA

(57) ABSTRACT

The invention relates to an antimicrobial surface, in particular a surface functionalised with a peptide comprising an antimicrobial moiety. The invention comprises a surface functionalised with a peptide comprising an antimicrobial moiety and a binder moiety, wherein the peptide is immobilized on the surface by electrostatic interactions between the binder moiety and the surface. Further provided is a medical device, a peptide and a method for the immobilization of a peptide.

Figure 1:
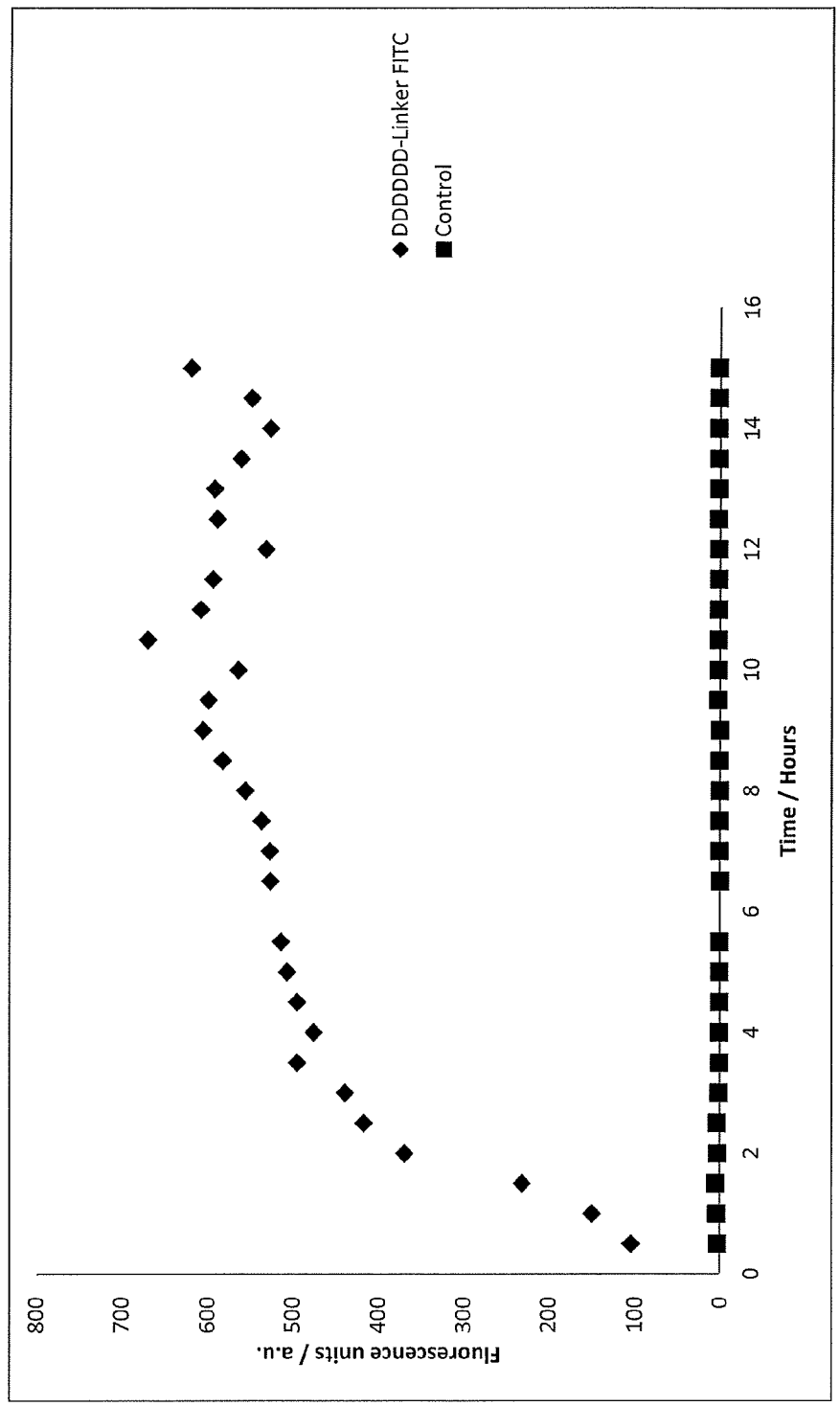

18 Claims, 7 Drawing Sheets
Specification includes a Sequence Listing.

(56) References Cited

OTHER PUBLICATIONS

Hisako Saido-Sakanaka, et al., "In vitro and in vivo activity of antimicrobial peptides synthesized based on the insect defense", Peptides, vol. 25, No. 1, Jan. 1, 2004, pp. 19-27.
Journal of the American Chemical Society; vol. 125, 2003, KI Sano & K Shiba, A hexapeptide motif that electrostatically binds to the surface of titanium, 14234-14235.
Journal of Materials Science: Materials in Medicine, vol. 21, 2010. Y Liu, et al, Peptide aptarners against titanium-based implants identified through phage display, 1103-1107.

* cited by examiner

SEQUENCE LISTING

```
<160> NUMBER OF SEQ ID NOS: 38

<210> SEQ ID NO 1
<211> LENGTH: 9
<212> TYPE: PRT
<213> ORGANISM: Artificial Sequence
<220> FEATURE:
<223> OTHER INFORMATION: peptide synthesis

<400> SEQUENCE: 1

Arg Lys Leu Pro Asp Ala Gly Gly Gly
1               5

<210> SEQ ID NO 2
<211> LENGTH: 11
<212> TYPE: PRT
<213> ORGANISM: Artificial Sequence
<220> FEATURE:
<223> OTHER INFORMATION: peptide synthesis

<400> SEQUENCE: 2

Arg Arg Tyr Ile Gly Arg Gly Tyr Ile Arg Arg
1               5                   10

<210> SEQ ID NO 3
<211> LENGTH: 9
<212> TYPE: PRT
<213> ORGANISM: Artificial Sequence
<220> FEATURE:
<223> OTHER INFORMATION: peptide synthesis

<400> SEQUENCE: 3

Arg Leu Tyr Leu Arg Ile Gly Arg Arg
1               5

<210> SEQ ID NO 4
<211> LENGTH: 9
<212> TYPE: PRT
<213> ORGANISM: Artificial Sequence
<220> FEATURE:
<223> OTHER INFORMATION: peptide synthesis

<400> SEQUENCE: 4
```

```
Cys Arg Val Arg Gly Gly Arg Cys Ala
1               5

<210> SEQ ID NO 5
<211> LENGTH: 6
<212> TYPE: PRT
<213> ORGANISM: Artificial Sequence
<220> FEATURE:
<223> OTHER INFORMATION: peptide synthesis

<400> SEQUENCE: 5

Arg Arg Arg Arg Arg Arg
1               5

<210> SEQ ID NO 6
<211> LENGTH: 23
<212> TYPE: PRT
<213> ORGANISM: Artificial Sequence
<220> FEATURE:
<223> OTHER INFORMATION: peptide synthesis

<400> SEQUENCE: 6

Gly Arg Arg Arg Arg Arg Arg Gly Ala Leu Ala Gly Arg Arg Arg
1               5                   10                  15

Arg Arg Gly Ala Leu Ala Gly
            20

<210> SEQ ID NO 7
<211> LENGTH: 11
<212> TYPE: PRT
<213> ORGANISM: Artificial Sequence
<220> FEATURE:
<223> OTHER INFORMATION: peptide synthesis

<400> SEQUENCE: 7

Cys Arg Leu Tyr Leu Arg Ile Gly Arg Arg Cys
1               5                   10

<210> SEQ ID NO 8
<211> LENGTH: 25
<212> TYPE: PRT
<213> ORGANISM: Artificial Sequence
<220> FEATURE:
<223> OTHER INFORMATION: peptide synthesis

<400> SEQUENCE: 8

Cys Gly Arg Arg Arg Arg Arg Gly Ala Leu Ala Gly Arg Arg
1               5                   10                  15

Arg Arg Arg Gly Ala Leu Ala Gly Cys
            20                  25

<210> SEQ ID NO 9
<211> LENGTH: 10
<212> TYPE: PRT
<213> ORGANISM: Artificial Sequence
<220> FEATURE:
<223> OTHER INFORMATION: peptide synthesis

<400> SEQUENCE: 9

Cys Arg Val Arg Gly Gly Arg Cys Ala Cys
1               5                   10

<210> SEQ ID NO 10
<211> LENGTH: 8
<212> TYPE: PRT
<213> ORGANISM: Artificial Sequence
```

<220> FEATURE:
<223> OTHER INFORMATION: peptide synthesis

<400> SEQUENCE: 10

Cys Arg Arg Arg Arg Arg Cys
1               5

<210> SEQ ID NO 11
<211> LENGTH: 13
<212> TYPE: PRT
<213> ORGANISM: Artificial Sequence
<220> FEATURE:
<223> OTHER INFORMATION: peptide synthesis

<400> SEQUENCE: 11

Cys Arg Arg Tyr Ile Gly Arg Gly Tyr Ile Arg Arg Cys
1               5                   10

<210> SEQ ID NO 12
<211> LENGTH: 6
<212> TYPE: PRT
<213> ORGANISM: Artificial Sequence
<220> FEATURE:
<223> OTHER INFORMATION: peptide synthesis

<400> SEQUENCE: 12

Arg Lys Leu Pro Asp Ala
1               5

<210> SEQ ID NO 13
<211> LENGTH: 12
<212> TYPE: PRT
<213> ORGANISM: Artificial Sequence
<220> FEATURE:
<223> OTHER INFORMATION: peptide synthesis

<400> SEQUENCE: 13

Arg Lys Leu Pro Asp Ala Arg Lys Leu Pro Asp Ala
1               5                   10

<210> SEQ ID NO 14
<211> LENGTH: 7
<212> TYPE: PRT
<213> ORGANISM: Artificial Sequence
<220> FEATURE:
<223> OTHER INFORMATION: peptide synthesis

<400> SEQUENCE: 14

Glu Glu Glu Glu Glu Glu Glu
1               5

<210> SEQ ID NO 15
<211> LENGTH: 7
<212> TYPE: PRT
<213> ORGANISM: Artificial Sequence
<220> FEATURE:
<223> OTHER INFORMATION: peptide synthesis

<400> SEQUENCE: 15

Asp Asp Asp Asp Asp Asp Asp
1               5

<210> SEQ ID NO 16
<211> LENGTH: 18
<212> TYPE: PRT
<213> ORGANISM: Artificial Sequence
<220> FEATURE:

<223> OTHER INFORMATION: peptide synthesis

<400> SEQUENCE: 16

Arg Arg Ile Tyr Gly Arg Gly Tyr Ile Arg Arg Asp Asp Asp Asp
1               5                   10                  15

Asp Asp

<210> SEQ ID NO 17
<211> LENGTH: 18
<212> TYPE: PRT
<213> ORGANISM: Artificial Sequence
<220> FEATURE:
<223> OTHER INFORMATION: peptide synthesis

<400> SEQUENCE: 17

Arg Arg Ile Tyr Gly Arg Gly Tyr Ile Arg Arg Glu Glu Glu Glu
1               5                   10                  15

Glu Glu

<210> SEQ ID NO 18
<211> LENGTH: 20
<212> TYPE: PRT
<213> ORGANISM: Artificial Sequence
<220> FEATURE:
<223> OTHER INFORMATION: peptide synthesis

<400> SEQUENCE: 18

Arg Arg Ile Tyr Gly Arg Gly Tyr Ile Arg Arg Arg Lys Leu Pro Asp
1               5                   10                  15

Ala Gly Gly Gly
            20

<210> SEQ ID NO 19
<211> LENGTH: 16
<212> TYPE: PRT
<213> ORGANISM: Artificial Sequence
<220> FEATURE:
<223> OTHER INFORMATION: peptide synthesis

<400> SEQUENCE: 19

Arg Leu Tyr Leu Arg Ile Gly Arg Arg Asp Asp Asp Asp Asp Asp
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: peptide synthesis

<400> SEQUENCE: 20

Arg Leu Tyr Leu Arg Ile Gly Arg Arg Glu Glu Glu Glu Glu Glu
1               5                   10                  15

<210> SEQ ID NO 21
<211> LENGTH: 18
<212> TYPE: PRT
<213> ORGANISM: Artificial Sequence
<220> FEATURE:
<223> OTHER INFORMATION: peptide synthesis

<400> SEQUENCE: 21

Arg Leu Tyr Leu Arg Ile Gly Arg Arg Arg Lys Leu Pro Asp Ala Gly
1               5                   10                  15

Gly Gly

<210> SEQ ID NO 22
<211> LENGTH: 16
<212> TYPE: PRT
<213> ORGANISM: Artificial Sequence
<220> FEATURE:
<223> OTHER INFORMATION: peptide synthesis

<400> SEQUENCE: 22

Cys Arg Val Arg Gly Gly Arg Cys Ala Asp Asp Asp Asp Asp Asp Asp
1               5                   10                  15

<210> SEQ ID NO 23
<211> LENGTH: 16
<212> TYPE: PRT
<213> ORGANISM: Artificial Sequence
<220> FEATURE:
<223> OTHER INFORMATION: peptide synthesis

<400> SEQUENCE: 23

Cys Arg Val Arg Gly Gly Arg Cys Ala Glu Glu Glu Glu Glu Glu Glu
1               5                   10                  15

<210> SEQ ID NO 24
<211> LENGTH: 18
<212> TYPE: PRT
<213> ORGANISM: Artificial Sequence
<220> FEATURE:
<223> OTHER INFORMATION: peptide synthesis

<400> SEQUENCE: 24

Cys Arg Val Arg Gly Gly Arg Cys Ala Arg Lys Leu Pro Asp Ala Gly
1               5                   10                  15

Gly Gly

<210> SEQ ID NO 25
<211> LENGTH: 13
<212> TYPE: PRT
<213> ORGANISM: Artificial Sequence
<220> FEATURE:
<223> OTHER INFORMATION: peptide synthesis

<400> SEQUENCE: 25

Arg Arg Arg Arg Arg Arg Asp Asp Asp Asp Asp Asp Asp
1               5                   10

<210> SEQ ID NO 26
<211> LENGTH: 13
<212> TYPE: PRT
<213> ORGANISM: Artificial Sequence
<220> FEATURE:
<223> OTHER INFORMATION: peptide synthesis

<400> SEQUENCE: 26

Arg Arg Arg Arg Arg Arg Glu Glu Glu Glu Glu Glu Glu
1               5                   10

<210> SEQ ID NO 27
<211> LENGTH: 15
<212> TYPE: PRT
<213> ORGANISM: Artificial Sequence
<220> FEATURE:
<223> OTHER INFORMATION: peptide synthesis

<400> SEQUENCE: 27

Arg Arg Arg Arg Arg Arg Arg Lys Leu Pro Asp Ala Gly Gly Gly
1               5                   10                  15

<210> SEQ ID NO 28
<211> LENGTH: 11
<212> TYPE: PRT
<213> ORGANISM: Artificial Sequence
<220> FEATURE:
<223> OTHER INFORMATION: peptide synthesis

<400> SEQUENCE: 28

Arg Arg Ile Tyr Gly Arg Gly Tyr Ile Arg Arg
1               5                   10

<210> SEQ ID NO 29
<211> LENGTH: 9
<212> TYPE: PRT
<213> ORGANISM: Artificial Sequence
<220> FEATURE:
<223> OTHER INFORMATION: peptide synthesis

<400> SEQUENCE: 29

Pro Ala Cys Ile Gly Glu Arg Arg Tyr
1               5

<210> SEQ ID NO 30
<211> LENGTH: 11
<212> TYPE: PRT
<213> ORGANISM: Artificial Sequence
<220> FEATURE:
<223> OTHER INFORMATION: peptide synthesis

<400> SEQUENCE: 30

Gly Thr Cys Ile Tyr Gln Arg Leu Asn Ala Phe
1               5                   10

<210> SEQ ID NO 31
<211> LENGTH: 11
<212> TYPE: PRT
<213> ORGANISM: Artificial Sequence
<220> FEATURE:
<223> OTHER INFORMATION: peptide synthesis

<400> SEQUENCE: 31

Cys Ala Thr Arg Glu Ser Leu Ser Gly Val Cys
1               5                   10

<210> SEQ ID NO 32
<211> LENGTH: 11
<212> TYPE: PRT
<213> ORGANISM: Artificial Sequence
<220> FEATURE:
<223> OTHER INFORMATION: peptide synthesis

<400> SEQUENCE: 32

Gly Thr Cys Gly Leu Pro Gly Thr Lys Cys Cys
1               5                   10

<210> SEQ ID NO 33
<211> LENGTH: 11
<212> TYPE: PRT
<213> ORGANISM: Artificial Sequence
<220> FEATURE:
<223> OTHER INFORMATION: peptide synthesis

<400> SEQUENCE: 33

Cys Ile Ser Glu Lys Thr Thr Asp Gly His Cys

```
<210> SEQ ID NO 34
<211> LENGTH: 9
<212> TYPE: PRT
<213> ORGANISM: Artificial Sequence
<220> FEATURE:
<223> OTHER INFORMATION: peptide synthesis

<400> SEQUENCE: 34

Cys Arg Val Arg Gly Gly Arg Cys Ala
1               5

<210> SEQ ID NO 35
<211> LENGTH: 8
<212> TYPE: PRT
<213> ORGANISM: Artificial Sequence
<220> FEATURE:
<223> OTHER INFORMATION: peptide synthesis

<400> SEQUENCE: 35

Glu Glu Glu Glu Glu Glu Glu Glu
1               5

<210> SEQ ID NO 36
<211> LENGTH: 19
<212> TYPE: PRT
<213> ORGANISM: Artificial Sequence
<220> FEATURE:
<223> OTHER INFORMATION: peptide synthesis

<400> SEQUENCE: 36

Arg Arg Ile Tyr Gly Arg Gly Tyr Ile Arg Arg Glu Glu Glu Glu
1               5                   10                  15

Glu Glu Glu

<210> SEQ ID NO 37
<211> LENGTH: 17
<212> TYPE: PRT
<213> ORGANISM: Artificial Sequence
<220> FEATURE:
<223> OTHER INFORMATION: peptide synthesis

<400> SEQUENCE: 37

Arg Arg Ile Tyr Gly Arg Gly Tyr Ile Arg Arg Arg Lys Leu Pro Asp
1               5                   10                  15

Ala

<210> SEQ ID NO 38
<211> LENGTH: 16
<212> TYPE: PRT
<213> ORGANISM: Artificial Sequence
<220> FEATURE:
<223> OTHER INFORMATION: peptide synthesis

<400> SEQUENCE: 38

Arg Arg Ile Tyr Gly Arg Gly Tyr Ile Arg Arg Lys Leu Pro Asp Ala
1               5                   10                  15
```

ANTIMICROBIAL SURFACE

The present invention relates to an antimicrobial surface, in particular a surface functionalized with a peptide comprising an antimicrobial moiety.

The treatment of trauma patients frequently requires the use of implanted prosthetic materials to stabilize fractures in an infection-prone environment. The development of infection around prostheses is not only a major cause of implant failure, but also contributes to morbidity. The current treatment of infection relies on the administration of antibiotics to eradicate bacteria and limit the spread of infection to adjacent tissues and elsewhere in the body. However, many infections, especially bone and prosthetic infections, involve the formation of a microbial biofilm. Biofilms inhibit the penetration of antimicrobial agents and, since the cells within the biofilm are relatively quiescent, the antimicrobial effect of such agents is decreased. The formation of biofilms is responsible for implant failure and extrusion. Resistance of bacteria to antibiotics is a further problem.

Coatings made from antibiotics and modified antibiotic structures have been used in implants. However, due to patient intolerance it is unlikely that these coatings can be easily used in the clinic. Furthermore, antibiotic-containing coatings do not address the obstacle of antibiotic resistance. Silver nanoparticles have also been used for antimicrobial activity, but further studies have demonstrated that these nanoparticles display significant levels of cytotoxicity.

EP2399618A relates to an antimicrobial medical device, wherein the antimicrobial peptide is attached to the silane surface of the medical device.

Alternative methods of treating and preventing bacterial colonization and infection of implants are therefore desperately needed.

The present invention has been devised with these issues in mind.

According to a first aspect of the present invention there is provided a surface functionalized with a peptide comprising an antimicrobial moiety and a binder moiety, wherein the peptide is immobilized on the surface by electrostatic interactions between the binder moiety and the surface.

The binder moiety tethers the peptide to the surface via electrostatic interactions. It will therefore be appreciated that the binder moiety will be chosen according to the nature of the surface. In some embodiments, the binder moiety is a peptide having no more than 20 amino acids. In some further embodiments, the binder moiety is a peptide having from 2 to 15 amino acids, from 4 to 10 amino acids, or from 6 to 9 amino acids.

The term "electrostatic interaction" will be understood to mean an interaction between a charged group of one substrate and an oppositely charged group of another substrate. Further details with regards to electrostatic interactions will be known to the skilled addressee and can be found in common textbooks (e.g. Stryer, Biochemistry, W.H. Freeman and Co Ltd 2002).

In some embodiments, the binder moiety has a net negative charge. A negative charge may enable the binder moiety to associate more strongly with positive ions found in some surfaces, for example hydroxyapatite. In some embodiments, the binder moiety comprises at least one, at least 3 or at least 5 acidic amino acid residues. The acidic amino acid residues may be aspartic acid or glutamic acid residues, or a mixture thereof.

In further embodiments, the binder moiety comprises at least 5, at least 6 or at least 7 aspartic acid (D) and/or glutamic acid (E) residues. The aspartic acid and/or glutamic acid residues may be consecutive or they may be spaced from each other by one or more other amino acids. Alternatively, the aspartic acid and/or glutamic acid residues may be arranged in groups of at least 2, at least 3 or at least 4 aspartic acid and/or glutamic acid residues, the groups being spaced from each other by one or more other amino acids.

In some embodiments, the binder moiety comprises at least 5, at least 6 or at least 7 consecutive aspartic acid (D) and/or glutamic acid (E) residues.

In some embodiments, the binder moiety comprises or consists of a sequence of from consecutive D residues has been found to associate strongly with surfaces made of hydroxyapatite and titanium.

In other embodiments, the binder moiety comprises a sequence of at least 5, at least 6 or at least 7 consecutive glutamic acid (E) residues. In some embodiments, the binder moiety comprises or consists of a sequence of from 5 to 10, from 6 to 9 or from 7 to 8 consecutive E residues. Such sequences are particularly effective at binding to hydroxyapatite.

In some embodiments, the binder moiety comprises or consists of the sequence RKLPDAGGG (SEQ ID NO: 1). This sequence has been found to be effective at binding to the surface of titanium.

The binder moiety may comprise one or more of the sequences described above. For example, the binder moiety may comprise one or more of the sequences selected from RKLPDAGGG (SEQ ID NO: 1), $(D)_{5-10}$, and $(E)_{5-10}$, or any combination thereof.

The antimicrobial moiety may have antibacterial, antiviral and/or antifungal activity. In some embodiments, the antimicrobial moiety is antibacterial. The antimicrobial moiety may have a bacteriostatic or a bactericidal effect against Gram-positive bacteria, Gram-negative bacteria, or both. In some embodiments, the antimicrobial moiety is effective against human or animal pathogens such as *E. coli, S. aureus* and *P. aeruginosa*.

In some embodiments, the antimicrobial moiety, or the peptide comprising the antimicrobial moiety, has a minimum inhibitory concentration of no more than 10 mg/ml, no more than 5 mg/ml, no more than 2.5 mg/ml, no more than 1.25 mg/ml, no more than 1.0 mg/ml or no more than 0.5 mg/ml against *E. coli, S. aureus* and/or *P. aeruginosa*.

The antimicrobial moiety may be derived from a defensin. Defensins are small peptides expressed by epithelial and immune cells, and display antimicrobial activity against many Gram-positive and Gram-negative bacteria, fungi and viruses. The defensin may be an alpha, a beta or a gamma defensin. By "derived from" it will be understood that the antimicrobial moiety may contain a part or the whole of the amino comprises or consists of a defensin peptide sequence, or a functional variant or fragment thereof.

The term "variant" of a defensin peptide sequence will be understood to mean that the antimicrobial moiety comprises or consists of a sequence having at least 30%, at least 40%, at least 50%, at least 60%, at least 70%, at least 80% or at least 90% identity with the amino acid sequence of a defensin peptide.

The term "fragment" will be understood to mean that the antimicrobial moiety comprises or consists of a portion of a defensin peptide. The fragment may be at least 30%, at least 40%, at least 50%, at least 60%, at least 70%, at least 80% or at least 90% of the whole of the defensin peptide. The fragment may include the C-terminus or the N-terminus of the defensin peptide, or it may include neither terminus.

By "functional", it will be understood that the variant or fragment retains at least some of the antimicrobial activity of the defensin sequence from which it is derived. It will be appreciated that it may be possible to remove, add or replace one or more of the amino acids of a defensin peptide sequence to provide a variant or fragment which still displays antimicrobial activity. Indeed, a variant or fragment may have improved antimicrobial activity compared to its parent sequence. The skilled technician will know how to produce fragments and variants of known defensin sequences and test their antimicrobial properties using standard techniques. The skilled technician will also know how to calculate the percentage identity between two amino acid sequences using well-known sequence alignment tools such as ClustalW (Thompson et al., 1994, Nucleic Acids Research, 22, 4673-4680; Thompson et al., 1997, Nucleic Acids Research, 24, 4876-4882).

The antimicrobial moiety may be from 5 to 40 amino acids in length. In some embodiments, the antimicrobial moiety has at least 6, at least 8 or at least 10 amino acids (residues). In some embodiments, the antimicrobial moiety has no more than 30, no more than 20, no more than 15 or no more than 12 amino acids.

Antimicrobial peptides are known in the art. A skilled person may employ any known antimicrobial peptide as the antimicrobial moiety of the peptide of the present invention.

However, the inventors have found peptides incorporating one or more of the following characteristics to be useful.

The antimicrobial moiety may comprise at least 3, at least 4 or at least 5 amino acids having a positively charged side chain. The amino acids having a positively charged side chain may be arginine (R), histidine (H), lysine (K), or any combination thereof. The positively charged amino acids may be arranged consecutively, or they may be spaced apart from each other by one or more residues. Without wishing to be bound by theory, it is thought that the association of positive charges with a bacterial cell membrane may force pore formation and induce cell death.

In some embodiments, the antimicrobial moiety comprises at least 3 or at least 4 arginine residues. The arginine residues may be arranged consecutively, or they may be spaced apart from each other by one or more residues.

In some embodiments, the antimicrobial moiety comprises at least one sequence of 5 or more consecutive arginine residues.

In some embodiments, the antimicrobial moiety includes one or more hydrophobic and neutral amino acid residues. It is believed that the inclusion of hydrophobic and neutral residues confers broad spectrum activity. The antimicrobial moiety may include from 1 to 20, from 2 to 10 or from 3 to 6 hydrophobic amino acids. By "hydrophobic and neutral amino acid" we mean alanine (A), isoleucine (I), leucine (L), methionine (M), phenylalanine (F), tryptophan (W), tyrosine (Y), glycine (G), proline (P) or valine (V).

In some embodiments, the antimicrobial moiety comprises one or more hydrophilic amino acid residues. The antimicrobial moiety may include from 1 to 20, from 2 to 10 or from 3 to 6 hydrophilic amino acids. By "hydrophilic amino acid" we mean serine (S), threonine (T), asparagine (N), glutamine (Q), aspartic acid (D), cysteine (C) or glutamic acid (E).

In some embodiments, the antimicrobial moiety comprises at least 3 positively charged amino acids and at least one hydrophobic amino acid and, optionally, at least one hydrophilic amino acid. In some further embodiments, at least two of the positively charged amino acids are separated from each other by one or more hydrophobic and/or hydrophilic residues.

In some embodiments, the antimicrobial moiety comprises or consists of a sequence having the formula $$A_{(x)}B_{(y)}A_{(x)}B_{(y)},$$

wherein:
A is a positively charged amino acid;
B is a hydrophobic amino acid or a hydrophilic amino acid;
x is a number of from 1 to 10; and
y is a number of from 1 to 10.

In some embodiments, the antimicrobial moiety comprises a sequence having the formula $$A_{(x)}Z_{(w)}B_{(y)}Z_{(w)}A_{(x)}Z_{(w)}B_{(y)}Z_{(w)}A_{(x)} \text{ or the formula}$$
$$A_{(x)}B_{(y)}Z_{(w)}B_{(y)}A_{(x)}B_{(y)}Z_{(w)}B_{(y)}A_{(x)}$$

wherein:
A is a positively charged amino acid;
B is a hydrophobic amino acid;
C is a hydrophilic amino acid;
x is a number of from 1 to 6;
y is a number of from 1 to 6; and
z is a number of from 1 to 6.

In some embodiments, the antimicrobial moiety comprises or consists of the sequence RRYIGRGYIRR (SEQ ID NO: 2).

In some embodiments, the antimicrobial moiety comprises or consists of the sequence RLYLRIGRR (SEQ ID NO: 3).

In some embodiments, the antimicrobial moiety comprises or consists of the sequence CRVRGGRCA (SEQ ID NO: 4).

In some embodiments, the antimicrobial moiety comprises or consists of the sequence RRRRRR (SEQ ID NO: 5).

In some further embodiments, the antimicrobial moiety comprises or consists of the sequence GRRRRRRGA-LAGRRRRRRGALAG (SEQ ID NO: 6).

In some embodiments, the sequence of the antimicrobial moiety comprises a terminal cysteine residue. In further embodiments, the sequence of the antimicrobial moiety has a cysteine residue at each end. For example, the sequence RLYLRIGRR (SEQ ID NO: 3) may be modified by the inclusion of terminal cysteine residues to give the sequence CRLYLRIGRRC (SEQ ID NO: 7). In silica studies have suggested that the inclusion of cysteine residues may enable the antimicrobial moiety to reversibly cyclise through the formation of disulphide bridges, depending on the environment. Without wishing to be bound by theory, the present inventors hypothesise that the tertiary structure of the antimicrobial moiety may also influence the antimicrobial activity of the peptide. Combining a three-dimensional structure with positive charges in the antimicrobial moiety may help to increase the efficacy of the peptide.

Thus, in some embodiments, the antimicrobial moiety comprises or consists of a sequence having the formula C $A_{(x)}B_{(y)}A_{(x)}B_{(y)}C$, wherein:
A is a positively charged amino acid;
B is a hydrophobic amino acid or a hydrophilic amino acid;
x is a number of from 1 to 10;
y is a number of from 1 to 10; and
C is a cysteine residue.

In some embodiments, the antimicrobial moiety comprises or consists of the sequence CRLYLRIGRRC (SEQ ID NO: 7), CGRRRRRRGALAGRRRRRRGALAGC (SEQ ID NO: 8), CRVRGGRCAC (SEQ ID NO: 9), CRRRRRRC (SEQ ID NO: 10) or CRRYIGRGYIRRC (SEQ ID NO: 11).

These sequences may be considered to be "synthetic defensins", since they are similar in structure and function to naturally occurring defensins.

The binder moiety and the antimicrobial moiety may be continuous, in that the sequence of the antimicrobial moiety is joined directly to that of the binder moiety such that there are no amino acid residues separating the two moieties. It will be understood that the binder moiety may be joined to the C- or to the N-terminus of the antimicrobial moiety.

In some embodiments the binder moiety is joined to the C-terminus of the antimicrobial moiety.

In other embodiments the binder moiety is joined to the N-terminus of the antimicrobial moiety.

Alternatively, the peptide may further comprise a linker between the binder moiety and the antimicrobial moiety. The linker may be of any desired length, for example from 1 to 50 amino acids, from 2 to 20 amino acids or from 5 to 10 amino acids in length (e.g. 7 amino acids). A linker may advantageously allow the antimicrobial moiety freedom of movement and reduce steric hindrance when the peptide is bound to a surface.

The surface may be any surface which benefits from having antimicrobial activity. For example, the functionalized surface may comprise at least a portion of a surface of a desk, a worktop, a door, a handle or a railing, or any other object that comes into regular contact with humans or animals. In particular, the functionalized surface may comprise at least a portion of the exterior of a tool or piece of apparatus used in healthcare or food preparation. A surface functionalized with an antimicrobial peptide finds particular use in medicine, especially in medical devices.

In some embodiments, the surface is biocompatible. By "biocompatible", it will be understood that the surface is capable of existing within a human or animal body without having toxic or other deleterious effects on the human or animal. It is particularly preferred that the surface does not elicit an immune response. Suitable biocompatible materials include titanium or alloys thereof, hydroxyapatite, stainless steel, aluminium or alloys thereof, ceramics such as brushite and other calcium phosphates, bioactive glasses and polymers.

The surface may be functionalized with a plurality of antimicrobial peptides. The surface may be partially functionalized with the peptides of the invention, i.e. only a portion of the surface may be functionalized. In some embodiments, at least 40%, at least 50%, at least 60%, at least 70%, at least 80% or at least 90% of the surface is functionalized with the peptides. In some embodiments, the whole of the surface is functionalized.

The density of peptides on the surface may be at least 50, at least 60, at least 70, at least 80 or at least 90 micromolar per $cm^2$ of surface.

The skilled person may employ any number of combinations of peptides on the surface, which comprise a binder moiety and an antimicrobial moiety.

In some embodiments, there is provided a surface functionalized with at least one, at least two, at least three or at least five peptides comprising an antimicrobial moiety and a binder moiety, wherein each peptide differs from another by at least one amino acid.

The use of electrostatic interactions to bind the peptide to the surface is particularly advantageous since it allows the peptide to be released from the surface. Release of the peptide from the surface may be immediate, or it may be sustained, i.e. peptides may be released gradually over a period of time.

In some embodiments, the release of the peptide from the surface is maintained for at least 2 hours, at least 6 hours, at least 10 hours, at least 14 hours or at least 20 hours. In further embodiments, the peptide is released over a period of at least 1 day (24 hours), at least 3 days, at least 5 days or at least 7 days.

In further embodiments, the surface is functionalized by a first antimicrobial agent which is a peptide comprising a first antimicrobial moiety and a first binder moiety, and a second antimicrobial agent comprising a second antimicrobial moiety and a second binder moiety, wherein the first antimicrobial agent is immobilized on the surface by electrostatic interactions between the first binder moiety and the surface, and wherein the second antimicrobial agent is immobilized on the surface by covalent interactions between the second binder moiety and the surface. This arrangement is beneficial since the covalent interactions provide a surface which is permanently antimicrobial, while the electrostatic interactions provide a controlled release of the first peptide over time. This is particularly useful in implants.

The second antimicrobial agent may be covalently bound to the surface by any suitable method. The second binder moiety may be a peptide or a non-peptide. For example, surface by incorporating nitrogen atoms onto the surface (known as 'nitriding'). The second binder moiety may then be covalently coupled to a nitrogen atom by forming an amide bond. Other methods of covalently immobilizing peptides on surfaces will be known to those skilled in the art.

According to a second aspect of the present invention, there is provided a medical device comprising the surface of the first aspect of the invention.

The device may be an implant (e.g. a dental implant, a pacemaker, a cochlear implant or an orthopaedic implant), a prosthesis (e.g. a prosthetic hip or knee, or a component thereof) or a surgical instrument. Alternatively the device may be one or more contact lenses.

The functionalized surface may constitute a portion of or the whole of a surface of the device. In some embodiments, the entire device is made from a biocompatible material. Alternatively, the device may comprise a core and a biocompatible coating.

According to a third aspect of the invention, there is provided a peptide comprising an antimicrobial moiety, wherein the antimicrobial moiety comprises a sequence selected from the group consisting of RRIYGRGYIRR (SEQ ID NO: 28) and GRRRRRRGALAGRRRRRRGA-LAG (SEQ ID NO: 6).

This peptide may find use in the preparation of antimicrobial surfaces, particularly for use in medical devices. The peptide may further comprise a binder moiety for attaching the peptide to a surface. Suitable binder moieties include those described herein.

The peptide may be formed by solid-phase peptide synthesis (SPPS). Further details with regards to SPPS will be known to those skilled in the art and can be found in common textbooks (e.g. Stryer, Biochemistry, W.H. Freeman and Co Ltd, 2002).

It is to be appreciated that the peptide is not associated with a biological entity. For the purposes of this invention, "biological entity" may refer to a virus, for example a phage, bacteria and/or virus-like particles.

According to a fourth aspect of the invention, there is provided a method for the immobilization of a peptide as defined herein, on a surface, comprising contacting the surface with the peptide and allowing the peptide to bind to the surface.

In some embodiments there is provided a method for the immobilization of a peptide, as defined herein, on a surface, comprising contacting the surface with the peptide and allowing the peptide to bind to the surface electrostatically.

In another embodiment there is provided a method for the immobilization of at least 2 peptides as described herein, comprising contacting a surface with a first peptide and allowing the first peptide to covalently bind to the surface; and contacting the surface with a second peptide and allowing the peptide to electrostatically bind to the surface.

In order to allow the first peptide to covalently to the surface, the surface may first be modified such as by the introduction of thiol groups onto ceramics (R L Williams, M J Hadley, P J Jiang, P M Mendes, J Z Rappoport, L M Grover, Thiol modification of silicon-substituted hydroxyapatite nanocrystals facilitates fluorescent labelling and visualization of cellular internalization, Journal of Materials Chemistry B, 2013, 1, 4370-4378) or by thermally surface treating metals to introduce groups for covalent attachment.

Figure 2:
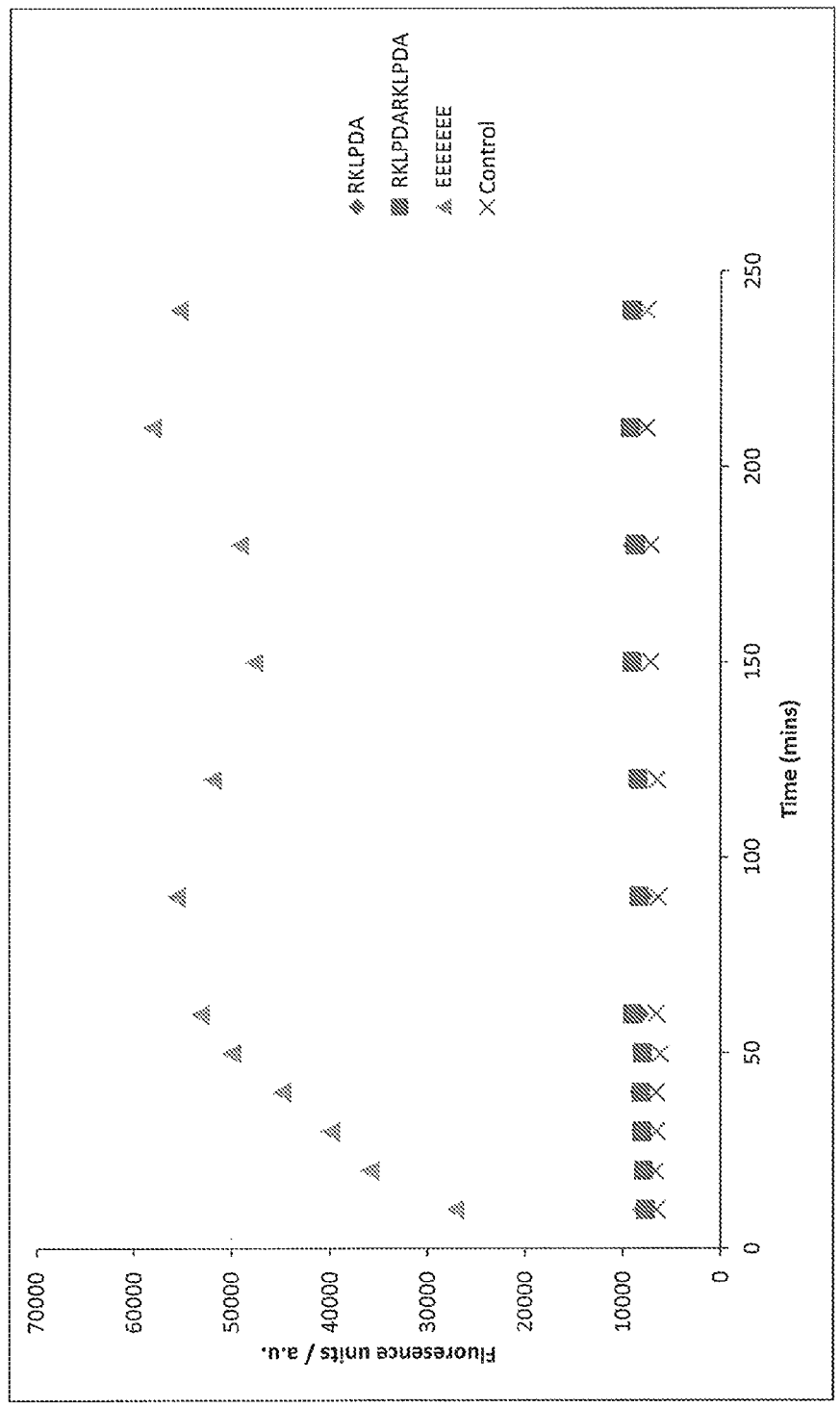
Figure 3:
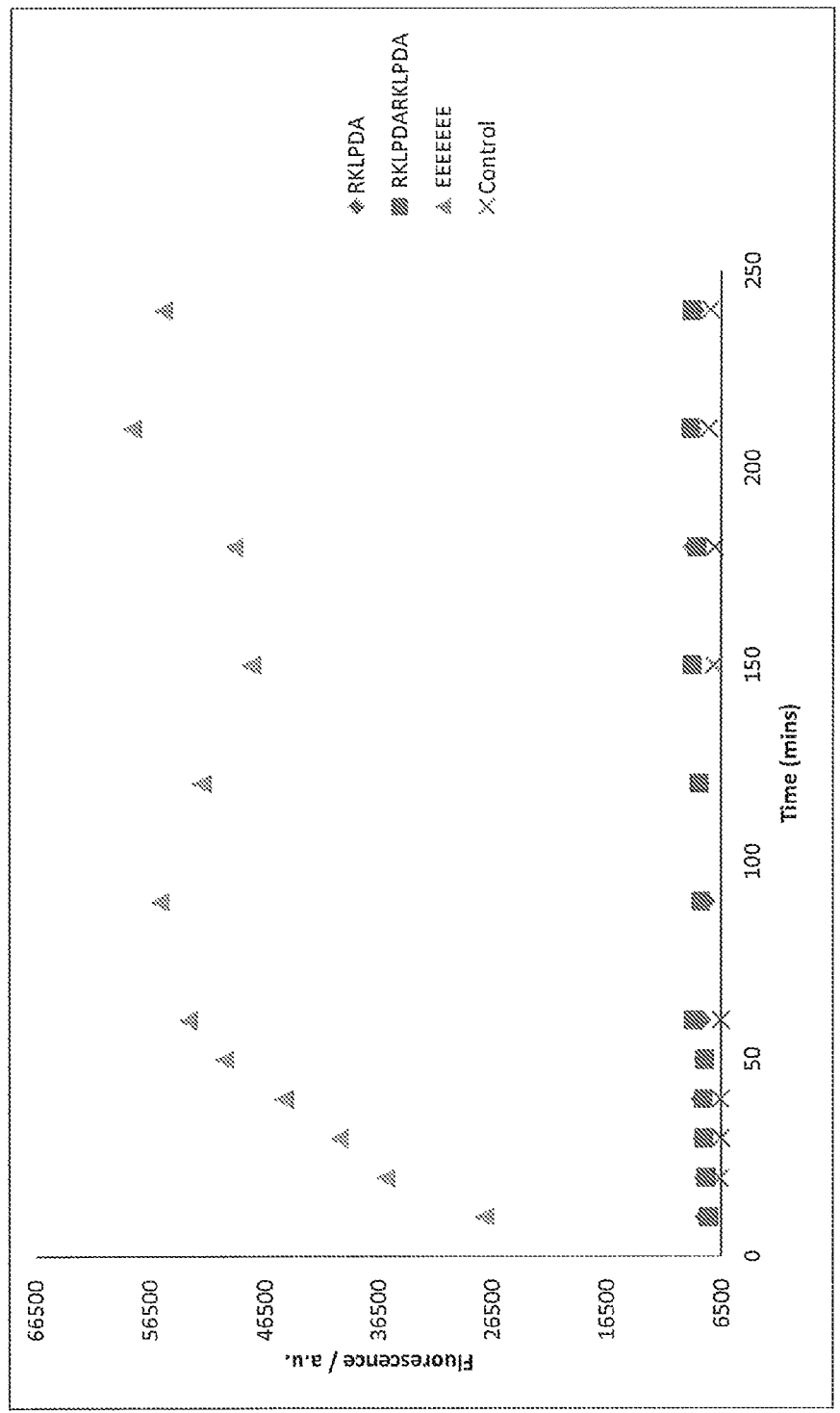
Figure 4:
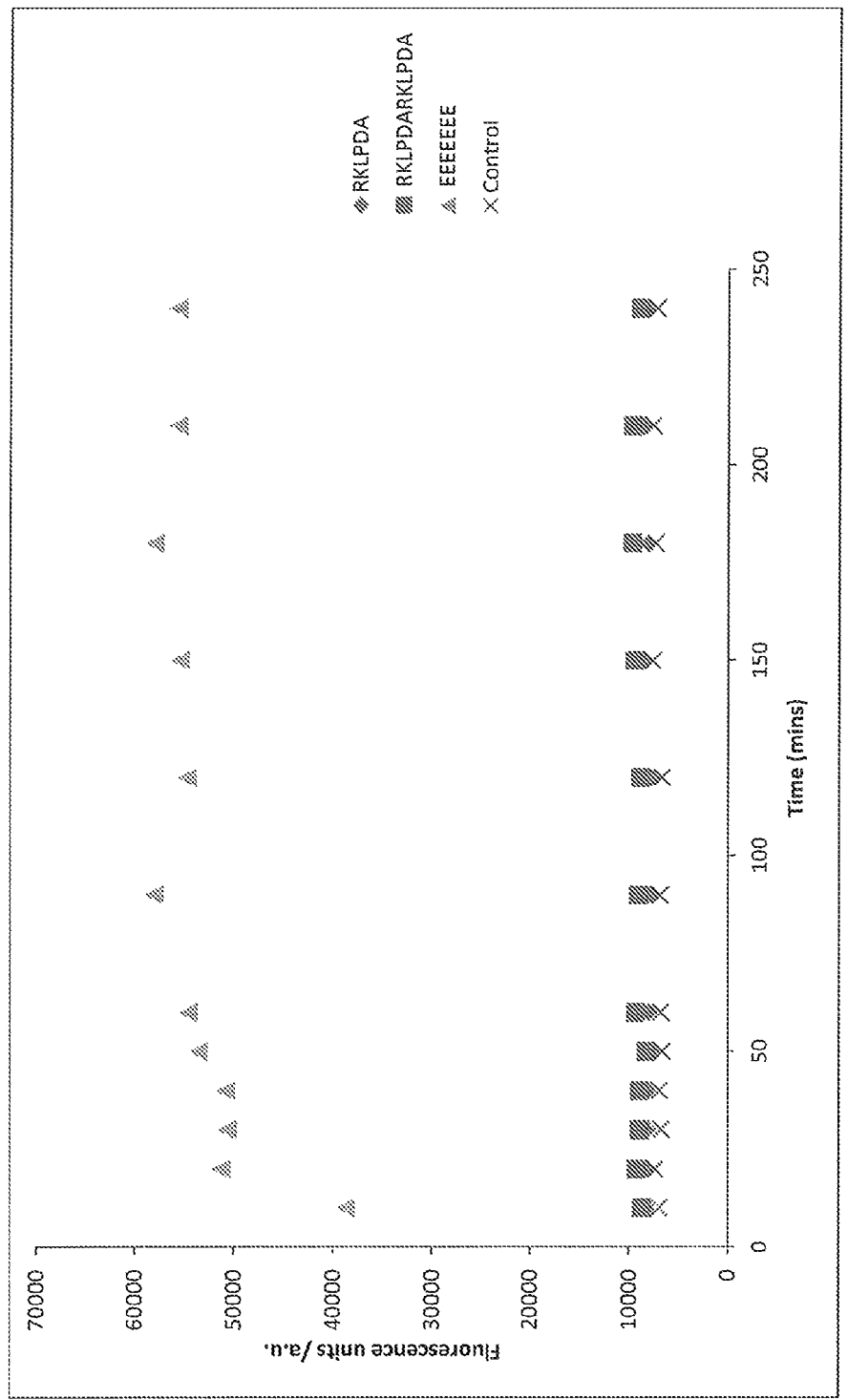
Figure 5:
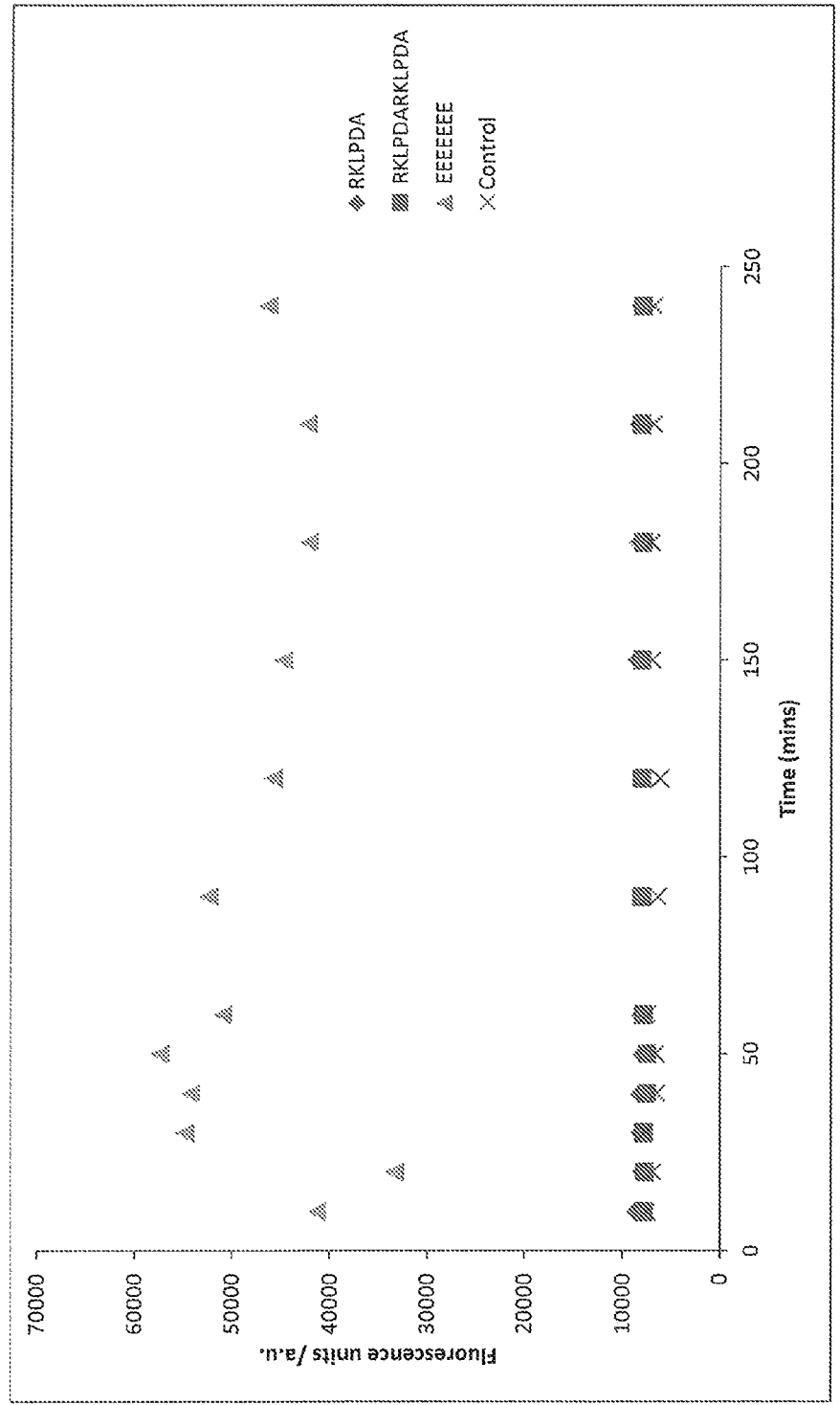
Figure 6:
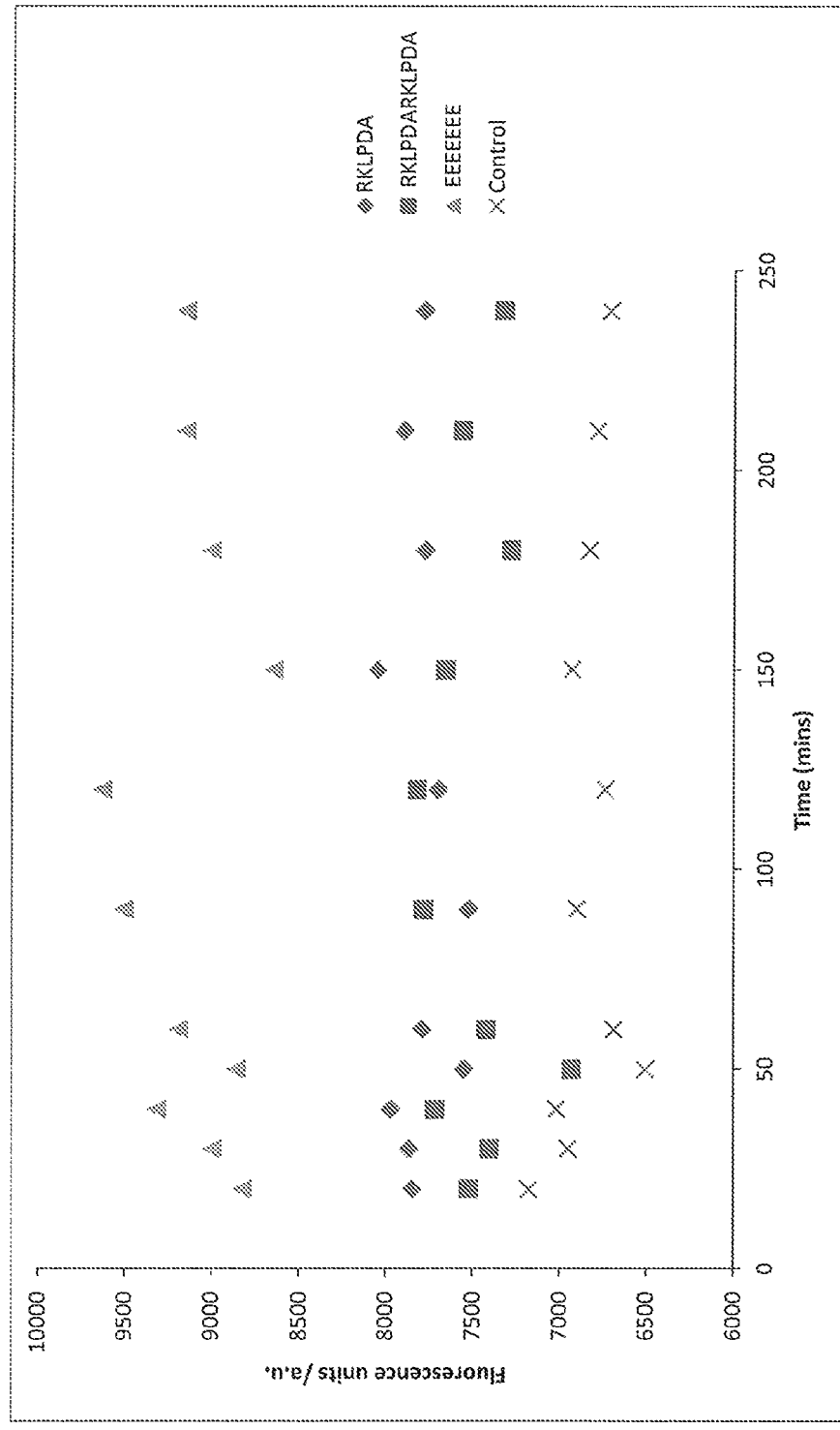
Figure 7:
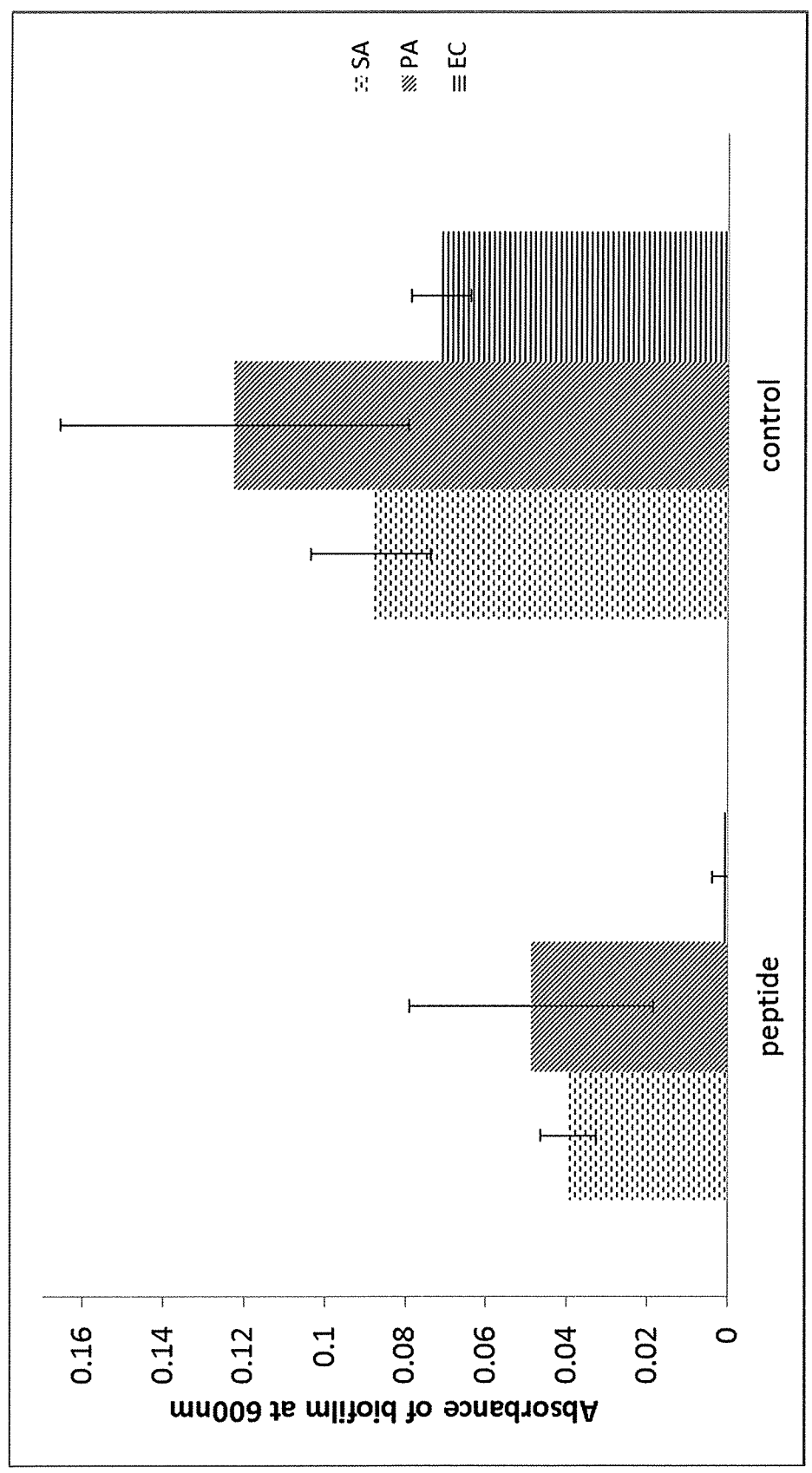

Embodiments of the invention will now be described by way of example, with reference to the accompanying Figures in which:

FIG. 1 is a plot showing the rate of release of the peptide DDDDDDD (SEQ ID NO: 15)-Linker-FITC from a hydroxyapatite surface; and FIG. 2 is a plot showing the rate of release of the peptides RKLPDA (SEQ ID NO: 12), RKLPDARKLPDA (SEQ ID NO: 13) and EEEEEEE (SEQ ID NO: 14) from a surface at 37° C. and pH 7; and FIG. 3 is a plot showing the rate of release of the peptides RKLPDA (SEQ ID NO: 12), RKLPDARKLPDA (SEQ ID NO: 13) and EEEEEEE (SEQ ID NO: 14) from a surface at 4° C. and pH 7; and FIG. 4 is a plot showing the rate of release of the peptides RKLPDA (SEQ ID NO: 12), RKLPDARKLPDA (SEQ ID NO: 13) and EEEEEEE (SEQ ID NO: 14) from a surface at room temperature and pH 7; and FIG. 5 is a plot showing the rate of release of the peptides RKLPDA (SEQ ID NO: 12), RKLPDARKLPDA (SEQ ID NO: 13) and EEEEEEE (SEQ ID NO: 14) from a surface at room temperature and pH 9; and FIG. 6 is a plot showing the rate of release of the peptides RKLPDA (SEQ ID NO: 12), RKLPDARKLPDA (SEQ ID NO: 13) and EEEEEEE (SEQ ID NO: 14) from a surface at room temperature and pH 4; and FIG. 7 is a graph comparing the growth of *E. coli*, *S. aureus* and *P. aeruginosa* in the presence and absence of an antimicrobial moiety.

EXAMPLES

Methodology

Peptide Synthesis

Peptides were synthesized using the solid phase peptide synthesis method (SPPS). This used resin beads as a solid phase support and Fmoc (Fluorenylmethyloxycarbonyl) protection chemistry. All the amino acids were protected on the amine group with an Fmoc protection group. The Fmoc group was cleaved using piperidine to give the free amine group on the amino acid. Once the Fmoc group was removed a second Fmoc protected amino acid was added to the resin. This coupling reaction uses HBTU (O-(Benzotriazol-1-yl)-N,N,N',N'-tetramethyluronium hexafluorophosphate) as a coupling reagent and was facilitated by DIPEA (diisopropylethylamine) which activated the carboxyl group and increased the reaction speed. This reaction gave rise to amide bond formation between the two amino acids and a dipeptide with a protected amine terminus was formed. This was then deprotected and reacted further until the full amino acid sequence was achieved.

The peptide sequences were confirmed by mass spectrometry and HPLC. The purity of the peptide decreased as the length of the amino acid sequences increased. Peptides of less than 10 amino acids were produced at high levels of purity (79-95%), while longer sequences had reduced purity (54-78%).

Formation of Hydroxyapatite

Hydroxyapatite was synthesized using the wet-chemical precipitation method. Saturated solutions of calcium nitrate and ammonium phosphate were formed and reacted together at 100° C. for 5 hours to give hydroxyapatite as a precipitate. This was then oven dried for 5 days and ground to create a fine powder. The powder was compressed into at 5 kN which gave a disk of 1.3 cm. The disk was then sintered at 1 100° C. for 2 hours to give a porous but stable hydroxyapatite sample of 0.85 cm.

Example 1: Binder-Surface Interactions

In order to ascertain whether the binder peptides DDDDDDD (SEQ ID NO: 15 (D7) interact with implant materials, the binder peptides were labelled with FITC for easy visualisation. Small hydroxyapatite disks (0.8 cm) and titanium squares (1 cm) were incubated in peptide solutions at pH 7 and room temperature. The samples were washed before imaging. The samples were then visualized using fluorescence microscopy to ascertain if adherence had occurred. A clear layer of FITC was seen across the surface of the hydroxyapatite disks and titanium squares, demonstrating that the peptides adhered well to the surfaces. This work established that the binder peptides interact with the surfaces A release study was carried out to ascertain the strength of adherence of the DDDDDDD (SEQ ID NO: 15)-Linker-FITC peptide to the hydroxyapatite surface. Disks of hydroxyapatite were incubated in 1 mg/ml peptide solutions for 1 hour and then washed thoroughly with PBS. The disk was then placed into a cuvette and surrounded with PBS solution (2 ml). The fluorescence of the solution around the disk was measured to ascertain the rate of peptide diffusion from the disk into the surrounding solution.

As can be seen in FIG. 1 the peptide was released from the hydroxyapatite block into the surrounding solution. This occurred at a fairly slow rate and increases in fluorescence were observed up to 10 hours. Following the release experiment the hydroxyapatite disks were washed with PBS, acetone, DMF and DCM and all washes measured for fluorescence but none was observed. This experiment demonstrates that the DDDDDDD (SEQ ID NO: 15) binder sequence provides a sustained release of peptide, making it suitable as a drug delivery binder.

Further release studies were carried out to ascertain the strength of adherence of the peptides RKLPDA (SEQ ID NO: 12), RKLPDARKLPDA (SEQ ID NO: 13) and EEEEEEE (SEQ ID NO: 14) to the surface under different temperatures and pH. Each peptide comprised a linker-FITC sequence for fluorescence. Surfaces were coated with peptide as described for FIG. 1. The peptide-coated disks were incubated in PBS or in a balanced buffer at a set pH. Aliquots of the solution surrounding the surface were taken out at set time points and the fluorescence of the peptide in the solution monitored to establish the rate of peptide diffusion from the disk into the surrounding solution.

As can be seen in FIG. 2 the peptide EEEEEEE (SEQ ID NO: 14) was released from the surface into the surrounding solution of pH 7 PBS when incubated at 37° C. The remaining peptides were not released under these conditions.

FIG. 3 shows that the peptide EEEEEEE (SEQ ID NO: 14) was released from the surface into the surrounding pH 7 PBS solution when incubated at 4° C. The other peptides were not released in these conditions.

In a balanced pH 7 buffer at room temperature the peptide EEEEEEE(SEQ ID NO: 141 was released, as shown in FIG. 4. However, the peptides RKLPDA (SEQ ID NO: 12) and RKLPDARKLPDA (SEQ ID NO: 13) were not released.

As shown in FIG. 5, in a balanced buffer at pH 9 and room temperature, the peptide EEEEEEE (SEQ ID NO: 14) was released into solution. The peptides RKLPDA (SEQ ID NO: 12) and RKLPDARKLPDA (SEQ ID NO: 13) were not released.

As can be seen in FIG. 6, at a pH of 4 and at room temperature release of all peptides at a fairly slow and constant rate was observed. Increased release was apparent for the peptide EEEEEEE (SEQ ID NO: 14) in comparison to the peptides RKLPDA (SEQ ID NO: 12) and RKLPDARKLPDA (SEQ ID NO: 13).

Example 2: Preparation of Antimicrobial Peptides

The antimicrobial moieties 1 (RRIYGRGYIRR) (SEQ ID NO: 28), 2 (RLYLRIGRR) (SEQ ID NO: 3), 3 (CRVRG-GRCA) (SEQ ID NO: 4) and 4(RRRRRR) (SEQ ID NO: 5) were combined with the binders A (DDDDDDD) (SEQ ID NO: 15), B (EEEEEEE) (SEQ ID NO: 14) and C (RKLP-DAGGG) (SEQ ID NO: 1) were to provide the following antimicrobial peptides:

| Peptide | Sequence |
| --- | --- |
| 1A | RRIYGRGYIRR-DDDDDDD (SEQ ID NO: 16) |
| 1B | RRIYGRGYIRR-EEEEEEE (SEQ ID NO: 16) |
| 1C | RRIYGRGYIRR-RKLPDAGGG (SEQ ID NO: 18) |
| 2A | RLYLRIGRR-DDDDDDD (SEQ ID NO: 19) |
| 2B | RLYLRIGRR-EEEEEEE (SEQ ID NO: 20) |
| 2C | RLYLRIGRR-RKLPDAGGG (SEQ ID NO: 21) |
| 3A | CRVRGGRCA-DDDDDDD (SEQ ID NO: 22) |
| 3B | CRVRGGRCA-EEEEEEE (SEQ ID NO: 23) |
| 3C | CRVRGGRCA-RKLPDAGGG (SEQ ID NO: 24) |
| 4A | RRRRRR-DDDDDDD (SEQ ID NO: 25) |
| 4B | RRRRRR-EEEEEEE (SEQ ID NO: 26) |
| 4C | RRRRRR-RKLPDAGGG (SEQ ID NO: 27) |

Example 3: Antimicrobial Assays

The antibacterial activity of various amino acid sequences was tested against *S. aureus, P. aeruginosa* and *E. coli*. The results are shown in Table 2.

TABLE 2

Minimum inhibitory concentration (MIC) of amino acid sequences in mg/mL

| Sequence | E. coli | S. aureus | P. aeruginosa |
| --- | --- | --- | --- |
| Antimicrobial moieties | | | |
| RLYLRIGRR (SEQ ID NO: 3) | 0.25 | 0.5 | 2 |
| RRIYGRGYIRR (SEQ ID NO: 28) | 1.25 | 2.5 | 2.5 |
| PACIGERRY (SEQ ID NO: 29) | 10 | 10 | 10 |
| GTCIYQRLNAF (SEQ ID NO: 30) | 10 | 10 | 10 |
| CATRESLSGVC (SEQ ID NO: 31) | 10 | 10 | 10 |
| GTCGLPGTKCC (SEQ ID NO: 32) | 10 | 5 | 5 |
| CISEKTTDGHC (SEQ ID NO: 33) | 10 | 10 | 10 |
| CRVRGGRCA (SEQ ID NO: 4) | 5 | 2.5 | 5 |
| RRRRRR (SEQ ID NO: 5) | 2.5 | 5 | 0.039 |
| Binder moieties | | | |
| EEEEEEEE (SEQ ID NO: 35) | none | none | none |
| RKLPDA (SEQ ID NO: 12) | none | none | none |
| Antimicrobial + binder moieties | | | |
| RRIYGRGYIRREEEEEEEE (SEQ ID NO: 36) | 5 | 5 | 10 |
| RRIYGRGYIRRRKLPDA (SEQ ID NO: 37) | 5 | 10 | 10 |

The data shown in Table 2 suggests that the incorporation of positive charges may be more important for antibacterial efficiency than the cysteine residues. This would indicate that the role of cysteine residues in natural defensins is primarily structural to maintain the correct formation of the peptide.

The MIC of the antimicrobial moiety RRIYGRGYIRR (SEQ ID NO: 28) was slightly higher than that of RLYL-RIGRR (SEQ ID NO: 3). RRIYGRGYIRR (SEQ ID NO: 28) exhibited consistent levels of an inhibitory effect against all the pathogens tested. The antimicrobial moiety RRRRRR (SEQ ID NO: 5) showed surprisingly high efficacy against *P. aeruginosa*, again suggesting that the incorporation of positive charges may be important for antibacterial activity. However, it may be possible that the mechanism of action for this sequence, which appears to be related to its charge, is different to the mode of action utilized by other peptides. The binding moieties alone (EEEEEEEE (SEQ ID NO: 35) and RKLPDA) had no antimicrobial activity.

Example 4: Ability of Peptide-Functionalized Surface to Inhibit Bacterial Growth The surface bound activity of the peptides was tested. Sample surfaces (hydroxyapatite discs and titanium plates) were incubated for 1 hour in a solution of RRIYGRGYIRR-EEEEEEE (SEQ ID NO: 36) or RRIYGRGYIR-RKLPDA (SEQ ID NO: 38) in PBS. The samples were then removed from the solution and washed with PBS. The surfaces were placed in a 24 well plate and suspended in LB broth (1 ml). The broth was then inoculated with bacteria (10 μl). The samples were incubated overnight and then the broth was removed and the surfaces checked for bacterial growth. In the peptide treated sample the solution was not as cloudy and the hydroxyapatite structures could be clearly seen, indicating a reduced bacterial growth rate compared to the untreated control.

The same assay was carried out to monitor the inhibition of biofilm formation by *E. coli, S. aureus* and *P. aeruginosa* on a titanium surface. Samples were prepared as described above. After the overnight incubation period the samples were removed from the solution and washed with PBS and then placed in fresh PBS. The samples were then vortexed to disrupt the biofilm and release the bacteria into the PBS which was then analyzed for bacterial growth. Complete inhibition of the *E. coli* biofilm and significant reductions in the biofilms of both *S. aureus* and *P. aeruginosa* was observed in the presence of the peptide (FIG. 7).

Example 5: Resistance Study

As the development of resistance is very important to antimicrobial drug targets the antimicrobial peptide sequence was tested for the development of a resistant strain emerging that could withstand the activity of the peptide. *E. coli, P. aeruginosa* and *S. aureus* were cultured for 7 days in the presence of low levels of the peptide (a quarter of the MIC for each different species). The peptide was gradually increased to 50% of the experimentally determined MIC over the time period. After 7 days the bacteria were seeded into a well plate containing peptide at a concentration of exactly 50% of the MIC and a 24 hour viability study was carried out. All the bacteria survived the low level concentration of the peptide with no observable inhibition of growth. After 24 hours the bacteria were crossed to fresh growth medium with the MIC level of peptide present and a 24 hour viability test was carried out. This showed that all the *E. coli* bacteria were dead and the *S. aureus* and the *P. aeruginosa* were inhibited but still alive. The bacteria were passaged again into growth medium containing double the MIC concentration and were subjected to a 24 hour viability test which showed that both the *S. aureus* and the *P. aeruginosa* were dead. This demonstrates that no resistance to the peptides develops over 7 days.

The invention claimed is:

1. A surface functionalized with a first peptide comprising a first antimicrobial moiety, and a first binder moiety, the first binder moiety having a net negative charge, and a second peptide comprising a second antimicrobial moiety and a second binder moiety, wherein the first peptide is immobilized on the surface by electrostatic interactions between the first binder moiety and the surface, the second peptide is immobilized on the surface by covalent interactions between the second binder moiety and the surface and wherein the first and the second peptide differ from each other by at least one amino acid.

2. The surface of claim 1, wherein the binder moiety is a peptide sequence of no more than 20 amino acids.

3. The surface of claim 1, wherein the first binder moiety comprises a sequence of at least 5 consecutive aspartic acid and/or glutamic acid residues.

4. The surface of claim 1, wherein the binder moiety comprises or consists of the sequence RKLPDAGGG (SEQ ID NO: 1).

5. The surface of claim 1, wherein the antimicrobial moiety is antibacterial.

6. The surface of claim 5, wherein the antimicrobial moiety has a minimum inhibitory concentration of no more than 5 mg/ml against *E. coli, S. aureus* and/or *P. aeruginosa*.

7. The surface of claim 1, wherein the antimicrobial moiety comprises a peptide sequence having at least 50% identity with the sequence of a defensin peptide.

8. The surface of claim 1, wherein the antimicrobial moiety is no more than 20 amino acids in length.

9. The surface of claim 1, wherein the antimicrobial moiety comprises at least 3 amino acids having a positively charged side chain selected from arginine (R), histidine (H) or lysine (K), or any combination thereof.

10. The surface of claim 1, wherein the antimicrobial moiety comprises a sequence of 5 or more consecutive arginine residues.

11. The surface of claim 1, wherein the antimicrobial moiety comprises a sequence having the formula $A_{(x)}B_{(y)}A_{(x)}B_{(y)}$, wherein:
   A is a positively charged amino acid;
   B is a hydrophobic amino acid and/or a hydrophilic amino acid;
   x is a number from 1 to 10; and
   y is a number from 1 to 10.

12. The surface of claim 11, wherein the antimicrobial moiety comprises or consists of the sequence RRYIGRGYIRR (SEQ ID NO: 2), RLYLRIGRR (SEQ ID NO: 3), CRVRGGRCA (SEQ ID NO: 4) or GRRRRRRGALAGRRRRRRGALAG (SEQ ID NO: 6).

13. The surface of claim 1, wherein the peptide further comprises a linker between the binder moiety and the antimicrobial moiety.

14. The surface of claim 1, wherein the surface is titanium or an alloy thereof, hydroxyapatite, stainless steel, aluminum or an alloy thereof, ceramic, glass or polymer.

15. The surface of claim 1, wherein the surface is capable of sustained release of the peptide over a period of at least 2 hours.

16. A peptide comprising an antimicrobial moiety, wherein the antimicrobial moiety comprises a sequence selected from the group consisting of RRIYGRGYIRR (SEQ ID NO: 28) and GRRRRRRGALAGRRRRRRGALAG (SEQ ID NO: 6).

17. A method for the immobilization of at least two peptides as defined in claim 2 comprising contacting a surface with a first peptide and allowing the first peptide to covalently bind to the surface; and
   contacting the surface with a second peptide and allowing the peptide to electrostatically bind to the surface.

18. A peptide comprising an antimicrobial moiety, wherein the antimicrobial moiety comprises a sequence selected from the group consisting of RRIYGRGYIRR (SEQ ID NO: 28), GTCIYQRLNAF (SEQ ID NO:30), and CISEKTTDGHC (SEQ ID NO: 33).

* * * * *